US008439845B2

(12) United States Patent
Folkerts et al.

(10) Patent No.: US 8,439,845 B2
(45) Date of Patent: May 14, 2013

(54) OBTAINING MEASUREMENTS OF MUSCLE REFLEXES FOR DIAGNOSIS OF PATIENT SYMPTOMS

(75) Inventors: Debra Janette Folkerts, Manhattan, KS (US); Karen Louise Finstrom McPhee, Williamsburg, VA (US); Gregory Ray Johnson, Nisswa, MN (US); Timothy Martin Gack, Walker, MN (US)

(73) Assignee: Uroval, Inc., Manhattan, KS (US)

( * ) Notice: Subject to any disclaimer, the term of this patent is extended or adjusted under 35 U.S.C. 154(b) by 1022 days.

(21) Appl. No.: 12/238,433

(22) Filed: Sep. 25, 2008

(65) Prior Publication Data

US 2009/0082830 A1 Mar. 26, 2009

Related U.S. Application Data

(60) Provisional application No. 60/975,056, filed on Sep. 25, 2007.

(51) Int. Cl.
*A61B 19/00* (2006.01)
*A61B 5/00* (2006.01)
*A61B 5/04* (2006.01)

(52) U.S. Cl.
USPC .......................... 600/557; 600/552; 600/546

(58) Field of Classification Search .............. 600/546, 600/545, 550, 590, 521–523, 421, 449, 459, 600/462, 493, 300, 330, 340, 339, 306, 591, 600/553, 595, 592

See application file for complete search history.

(56) References Cited

U.S. PATENT DOCUMENTS

| 3,933,147 A | 1/1976 | Du Vall et al. |
| 4,099,519 A | 7/1978 | Warren |
| 4,585,005 A | 4/1986 | Lue et al. |

(Continued)

FOREIGN PATENT DOCUMENTS

| DE | 19906140 | 7/2000 |
| FR | 2601254 | 7/1986 |

(Continued)

OTHER PUBLICATIONS

International Preliminary Report on Patentability for International (PCT) Patent Application No. PCT/US2008/077763, mailed Apr. 8, 2010.

(Continued)

*Primary Examiner* — Brian Szmal
*Assistant Examiner* — Mehari Kidanemariam
(74) *Attorney, Agent, or Firm* — Sheridan Ross P.C.

(57) ABSTRACT

A system and method is disclosed for measuring muscle reflexes (e.g., a bulbocavernosus reflex) as a tool for identifying/diagnosing dysfunctions (e.g., spinal cord abnormalities, bladder voiding dysfunction, and sexual organ dysfunction) non-invasively by using mechanical stimulation. The system and method includes a probe having a predetermined patient contacting portion, wherein when the contacting portion is moved into contact with a particular area of the patient (e.g., the patient's genitals), the contact induces a muscle reflex. The probe detects the pressure resulting from the contacting portion being abruptly and forcibly brought into contact with the particular area. Such detection is used to electronically initiate capture of electrical responses from a plurality of electrodes placed on the patient's skin in proximity to the particular area. Such electrical responses are processed to determine characteristics of the patient's reflexes of one or more muscles adjacent to the electrodes.

18 Claims, 6 Drawing Sheets

U.S. PATENT DOCUMENTS

| | | | |
|---|---|---|---|
| 4,674,517 A | | 6/1987 | Barnes et al. |
| 4,759,377 A | | 7/1988 | Dykstra |
| 4,817,628 A | * | 4/1989 | Zealear et al. .............. 600/554 |
| 4,881,526 A | | 11/1989 | Johnson et al. |
| 4,995,401 A | * | 2/1991 | Bunegin et al. .............. 600/561 |
| 5,016,635 A | | 5/1991 | Graupe |
| 5,058,602 A | | 10/1991 | Brody |
| 5,086,779 A | | 2/1992 | DeLuca et al. |
| 5,142,183 A | * | 8/1992 | Burgess et al. .............. 310/339 |
| 5,170,786 A | * | 12/1992 | Thomas et al. .............. 600/310 |
| 5,259,388 A | | 11/1993 | Eisman et al. |
| 5,263,489 A | * | 11/1993 | Johnson et al. .............. 600/546 |
| 5,318,039 A | | 6/1994 | Kadefors et al. |
| 5,329,194 A | * | 7/1994 | Dow et al. .................... 310/17 |
| 5,435,282 A | * | 7/1995 | Haber et al. ............ 128/200.16 |
| 5,505,208 A | | 4/1996 | Toormin et al. |
| 5,513,651 A | | 5/1996 | Cusimano et al. |
| 5,546,953 A | | 8/1996 | Garfield |
| 5,551,446 A | | 9/1996 | Chutkow et al. |
| 5,762,589 A | | 6/1998 | Parker |
| 5,775,331 A | | 7/1998 | Raymond et al. |
| 5,875,778 A | | 3/1999 | Vroegop |
| 5,875,788 A | | 3/1999 | Loren |
| 5,957,837 A | * | 9/1999 | Raab .............................. 600/300 |
| 6,047,202 A | | 4/2000 | Finneran et al. |
| 6,359,894 B1 | | 3/2002 | Hong et al. |
| 6,741,895 B1 | | 5/2004 | Gafni et al. |
| 6,862,480 B2 | * | 3/2005 | Cohen et al. .................... 607/41 |
| 7,004,904 B2 | | 2/2006 | Chalana et al. |
| 7,041,059 B2 | | 5/2006 | Chalana et al. |
| 7,087,022 B2 | | 8/2006 | Chalana et al. |
| 7,367,956 B2 | | 5/2008 | King |
| 7,467,119 B2 | | 12/2008 | Saidi et al. |
| 7,914,468 B2 | * | 3/2011 | Shalon et al. .................. 600/590 |
| 2004/0147920 A1 | | 7/2004 | Keidar |
| 2005/0043608 A1 | * | 2/2005 | Haj-Yousef ................... 600/407 |
| 2006/0004290 A1 | * | 1/2006 | Smith et al. .................... 600/459 |
| 2006/0089824 A1 | * | 4/2006 | Siekmeier et al. .............. 703/11 |
| 2006/0100668 A1 | | 5/2006 | Ben-David et al. |
| 2007/0099219 A1 | | 5/2007 | Teverovskiy et al. |
| 2007/0167812 A1 | * | 7/2007 | Lemmerhirt et al. ......... 600/459 |

FOREIGN PATENT DOCUMENTS

| | | |
|---|---|---|
| GB | 2284991 | 6/1995 |
| WO | WO 97/48446 | 12/1997 |
| WO | WO 02/065975 | 8/2002 |
| WO | WO 2007/089394 | 8/2007 |

OTHER PUBLICATIONS

U.S. Appl. No. 12/324,726, filed Nov. 26, 2008, Folkerts, et al.

Tackmann, et al. "The bulbocavernosus reflex in controls and patients with potency disorders", Sep. 17, 1986, pp. 147-152, available at http://www.ncbi.nlm.nih.gov/pubmed/3095091.

Prutchi, "A High-Resolution Large Array (HRLA) EMG System", Med. Eng. Phys., Sep. 1995, vol. 17, pp. 442-454.

Sarica, et al. "Bulbocavernosus reflex to somatic and visceral nerve stimulation in normal subjects and in diabetics with erectile impotence", Journal of Urology, Jul. 1987; 138(1): 55-8.

Ertekin, et al. "The value of somatosensory-evoked potentials and bulbocavernosus reflex in patients with impotence", Acta Neurol Scand., Jan. 1985; 71(1): 48-53.

Ziemann, et al. "Anal sphincter electromyography, bulbocavernosus reflex and pudendal somatosensory evoked potentials in diagnosis of neurogenic lumbosacral lesions with disorders of bladder and large intestine emptying and erectile dysfunction", Nervenarzt, Feb. 1996; 67(2): 140-6.

Lavoisier, et al. "Bulbocavernosus reflex: its validity as a diagnostic test of neurogenic impotence", Journal of Urology, Feb. 1989; 141(2): 311-4.

Vodusek, et al. "EMG, single fibre EMG and sacral reflexes in assessment of sacral nervous system lesions", Journal of Neurological Neurosurgery Psychiatry, Nov. 1982; 45(11): 1064-6.

Smith. "Scientists and Engineers Guide to Digital Signal Processing", 1997, Chapters 19 and 20, California Technical Publishing, San Diego, CA.

"RMS Algorithm", http://en.wikipedia,org/wiki/Root_mean_square, Jan. 15, 2009, pp. 1-9.

Kippers,"Electromyography (EMG)—Principles and Biological Bases", AN212 lecture, Mar. 14, 1999, pp. 1-13, The University of Queensland.

"First Magnes Whole Head System is Up and Running at Scripps Clinic", MSI Advances: Fall 96 Issue, 4-D Neuroimaging, 3 pages.

Tepley, et al. "Magnetoencephalography (MEG)", Neuromagnetism Lab at Henry Ford Hospital, http://rambutan.phy.oakland.edu/~meg/, 2003, pp. 1-47.

"Electrical Stimulation in Incontinence", Incontinence References, International Functional Electrical Stimulation Society, 2000, pp. 1-83.

Fowler, "A Neurologist's Clinical and Investigative Approach to Patients with Bladder, Bowel and Sexual Dysfunction", Neurology of Bladder, Bowel, and Sexual Dysfunction, vol. 1, 2001, pp. 1-6, chapter 1.

Podnar, et al. "Mechanically evoked bulbocavernosus reflex and pudendal somatosensory responses in children", European Journal of Physiology, 1996, pp. R293-R294, Springer-Verlag.

Shafik, "Perineal nerve stimulation for urinary sphincter control", Urological Research, vol. 22, No. 3/ May 1994, Springer Berlin/Heidelberg, pp. 151-155.

Vereecken, et al. "Electrophysiological exploration of the sacral conus", vol. 227, No. 3/Jun. 1982, pp. 135-144.

International Search Report for International (PCT) Application No. 08/77763, mailed Nov. 28, 2008.

Written Opinion for International (PCT) Application No. 08/77763, mailed Nov. 28, 2008.

Henry M.M. (1994) The role of pudendal nerve innervation in female pelvic floor function. Curr. Opin. Obstet. Gynecol. 6, 324-325.

Kaiho Y., Namima T., Uchi K., Nakagawa H., Aizawa M., and Orikasa S. (1999) [Electromyographic study of the striated urethral sphincter by using the bulbocavernosus reflex: study of the normal voluntary voiding and the involuntary sphincter relaxation]. Nippon Hinyokika Gakkai Zasshi 90, 893-900 (English Abstract Only).

Amarenco et al., "Dissociation between electrical and mechanical bulbocavernosus reflexes", Neurourology & Urodynamics, vol. 22(7), 2003, pp. 676-680.

Waldron et al.,"Evidence for motor neuropathy and reduced filling of the rectum in chronic intractable constipation," Gut, vol. 31, 1990, pp. 1284-1288.

Extended EP Search Report for EP Application No. 08834484.1, mailed Feb. 9, 2012, 11 pages.

Official Action for U.S. Appl. No. 12/324,726, mailed Dec. 8, 2011.

Official Action for European Patent Application No. 08834484.1, dated Sep. 11, 2012 4 pages.

* cited by examiner

OBTAINING MEASUREMENTS OF MUSCLE REFLEXES FOR DIAGNOSIS OF PATIENT SYMPTOMS

RELATED APPLICATIONS

The present application claims the benefit of U.S. Provisional Patent Application No. 60/975,056 filed Sep. 25, 2007 which is incorporated by reference herein in its entirety.

RELATED FIELD OF THE INVENTION

The present disclosure relates to obtaining and processing data indicative muscle reflexes for screening and/or diagnosing a patient, and especially for obtaining and processing data indicative of reflexes from the bulbospongiosus muscle. In particular, the present disclosure describes a novel electromechanical probe for stimulating the bulbospongiosus muscle, and consequently identifying a time of the stimulation so that electrical responses from electrodes on the patient's skin can be identified for analysis.

BACKGROUND

The bulbospongiosus muscle is one of the superficial muscles of the perineum. This muscle is innervated by the deep/muscular branch of the perineal nerve, which is a branch of the pudendal nerve. This muscle has a slightly different origin, insertion and function in males and females. In both sexes, however, bulbospongiosus muscle is important to normal sexual function and feelings, as well as urinary function. In males the bulbospongiosus muscle contributes to erection, ejaculation, and the feelings of orgasm. In females bulbospongiosus muscle closes the vagina and contributes to the feelings of orgasm.

The bulbocavernosus reflex (BCR) is a distinct, automatic (reflex) contraction of the rectum (part of the bowel) that occurs when the tip of the penis (in a man) or clitoris (in a woman) is squeezed or stimulated. In more technical terms, the bulbocavernosus reflex is a multi-synaptic reflex, and measurements of this reflex can provide indications of various neurological abnormalities in and around the pelvic floor, and the lower spinal region of a patient. For example, the integrity of afferent and efferent segments through sacral spinal segments (S2-S4) and pudendal nerve may be determined by such BCR measurements. Additionally, several levels of BCR abnormalities have been reported in cases with impotence when cauda equina or conus medullaris lesions are present, or when neurogenic bladder related to polyneuropathy is detected. Such BCR abnormalities appear as no BCR response, a prolonged latency in BCR response, or a temporal latency dispersion occurring in repetitive measurements. Moreover, a BCR response, if prolonged, can be an indication of pelvic nerve damage in patients with pelvic floor disorders.

It is known to use measurements of the BCR for diagnosis and treatment of various pelvic floor disorders, including those disorders mentioned above. Such measurements may be collected from, e.g., urethral and/or anal sphincters after stimulation of the dorsal nerve of the penis or clitoris via activation of electrodes appropriately attached to a patient. Additionally, such measurements have been obtained using EMG (electromyogram) testing. The following references are fully incorporated herein by reference for further description of EMG and the use of electrodes for diagnosing patient disorders:

U.S. Pat. No. 6,047,202 which discloses an electrode and array thereof for collecting surface electromyographic signals.

D. Prutchi in the publication "A High-Resolution Large Array (HRLA) EMG System" published September 1995 in Med. Eng. Phys., Vol. 17, 442-454. Prutchi describes a bracelet which may be wrapped about a body limb and which contains 256 surface electrodes to record the electrical activity of underlying muscles. The electrodes are arranged in eight groups of thirty-two electrode linear arrays directly connected to buffer boards in close proximity of the electrodes. Further processing of the electrical signals is performed to provide a desired signal analysis, in this instance primarily being concerned with the bidirectional propagation of a compound potential in a single muscle in the upper arm of a human subject or a histogram of total power contribution from active fibers in a subject muscle, both being presented in charted format.

U.S. Pat. No. 5,086,779 to DeLuca, et al., describes a back analysis system of plural electrodes coupled to a computer system for processing the signals and to provide graphical representations of results. DeLuca's invention relates primarily to isolating particular muscle groups by the use of support and restraint devices which limit the movement of the patient's torso in predetermined patterns correlated to the desired muscle groups. DeLuca's electrode array consists of separate electrodes individually placed at desired locations on a patient's back.

U.S. Pat. No. 5,058,602 to Brody describes a method of electromyographic scanning of paravertebral muscles comprising measuring electrical potentials bilaterally across segments of the spine. Readings are categorized into different patterns which are indicative of different muscular conditions. Brody suggests equipment useful within his described techniques as an available EMG scanner having electrodes spaced 2.5 cm apart and a computer component, but provides few details on the equipment or an indication of usefulness for isolating certain muscles or muscle groups.

U.S. Pat. No. 5,318,039 to Kadefors, et al., describes a method and apparatus for detecting electromyographic signals, processing them and providing an indication of the change of the signal from a predetermined norm. Kadefors' electrode system comprises three electrodes, one of which is a reference marker. This electronic apparatus, in essence, includes a sample and hold function in which current responses can be compared to earlier responses and an indication provided based on the differences detected.

U.S. Pat. No. 5,505,208 to Toormin, et al., describes a method for determining the status of back muscles wherein EMG signals are monitored from a number of electrodes placed in a pattern on a patient's back, the activity of each electrode is determined and the results stored. A database of results provides a standard from which comparisons can be made to determine deviations or abnormalities, as a device for the care and management of the patient's dysfunction.

U.S. Pat. No. 5,513,651 to Cusimano, et al., describes a portable electronic instrument for monitoring muscle activity, using standard ECG electrodes and a computer for analyzing the detected signals. The electrodes are applied individually at predetermined locations and a range of motion device is employed to generate signals related to a particular muscle group. Output plots are produced to provide an indication of results, apparently in the form of printouts of information reflecting any deviations from the norm of expected muscle activity.

Additional prior art references describing the use of the bulbocavernosus reflex for assessing patient dysfunctions are as follows, these references being fully incorporated herein by reference as well:

Sarica Y, Karacan I, "Bulbocavernosus reflex to somatic and visceral nerve stimulation in normal subjects and in diabetics with erectile impotence", Journal of Urology, July 1987; 138 (1): 55-8;

Ertekin C, Akyurekli O, Gurses A N, Turgut H, "The value of somatosensory-evoked potentials and bulbocavernosus reflex in patients with impotence", Acta Neurol Scand., January 1985; 71 (1): 48-53;

Ziemann U, Reimers C D. "Anal sphincter electromyography, bulbocavernosus reflex and pudendal somatosensory evoked potentials in diagnosis of neurogenic lumbosacral lesions with disorders of bladder and large intestine emptying and erectile dysfunction", Nervenarzt, February 1996; 67 (2): 140-6;

Lavoisier P, Proulx J, Courtois F, De Carufel F, "Bulbocavernosus reflex: its validity as a diagnostic test of neurogenic impotence", Journal of Urology, February 1989; 141 (2): 311-4;

Vodusek D B, Janko M, Lokar J., "EMG, single fibre EMG and sacral reflexes in assessment of sacral nervous system lesions", Journal of Neurological Neurosurgery Psychiatry, November 1982; 45 (11): 1064-6.

However, prior art procedures and apparatuses for obtaining such BCR measurements have been less than satisfactory, e.g., in their ease of use, and the discomfort caused to patients. Accordingly, it would be advantageous to have a non-invasive method and system for accurately detecting characteristics of the BCR response, such as latency in response, lack of response, abnormal reflex contractions, wherein such characteristics of the BCR are correlated with likely physiological and/or neurological dysfunctions.

SUMMARY

A system and method is disclosed herein for measuring muscle reflexes (e.g., a bulbocavernosus reflex) as a tool for identifying/diagnosing dysfunctions such as spinal cord abnormalities (e.g., in segments S2 thru S4), bladder voiding dysfunction, and sexual organ dysfunction. In particular, the novel screening system and method (referred to as a "screening system and method" herein) disclosed herein provides a non-invasive measurement of the muscle reflex using mechanical stimulation. Such non-invasive mechanical stimulation is advantageous because it is less painful to the patient than prior art measurement techniques, and in certain instances easier to obtain reflex measurements than prior art techniques for measuring a patient's muscle reflexes. More particularly, a probe is provided that includes a predetermined contacting portion for contacting the patient, wherein when the contacting portion of the probe is moved into contact with a particular area of the patient (e.g., the patient's genitals), the contact induces a reflex in one or more of the patient's muscles. Thus, the contacting portion of the probe provides a mechanical stimulus for inducing the patient reflex. In one embodiment, the probe detects the pressure resulting from the contacting portion of the probe being abruptly and forcibly brought into contact with the particular area of the patient's skin, wherein such detection is used to electronically initiate the capture of electrical responses from a plurality of electrodes placed on the patient's skin in proximity to the particular area. Such electrical responses can then be processed to provide characteristics of the patient's reflexes of one or more muscles adjacent to the electrodes.

In one embodiment of the probe, the patient contacting portion is detachable from the remainder of the probe so that for different patients different patient contacting portions are used. That is, the probe may be reusable with a plurality of patients except for the patient contacting portion which is replaceable between patients. Moreover, the patient contacting portion (or the probe itself if it is non-usable with different patients) may include an electronic device and non-volatile data storage for identifying whether the probe can be used for the data capture (and subsequent processing) of electrical responses indicative of muscle reflex contraction.

In one particularly important embodiment, the screening system and method disclosed herein measures the bulbocavernosus reflex response in units of milliseconds when this reflex is induced from the activation of the bulbospongiosus superficial muscle of the perineum via mechanical stimulation of the clitoris or penis. The resulting reflex measurements may be used for detecting abnormalities in the BCR such as no BCR response, a prolonged latency in BCR response, a prolonged BCR response, or a temporal latency dispersion occurring in repetitive measurements. As indicated above, such BCR abnormalities may be indicative of various patient dysfunctions, such as spinal cord damage in segments S2 through S4, urinary voiding dysfunctions, and/or sexual organ dysfunctions (e.g., impotence).

In one embodiment of the novel screening system and method disclosed herein, a prolonged bulbocavernosus reflex (e.g., more than 45 milliseconds), or an excessive latency in reflex response (e.g., more than 45 milliseconds) is considered a sign of neurological disease and/or neurological dysfunction. For example, a prolonged BCR response can be an indication of pelvic nerve damage in patients with pelvic floor disorders. Accordingly, results from the present screening system and method can be used in diagnosis and treatment of pelvic floor disorders.

The system and method disclosed herein includes components for EMG (electromyogram) testing to determine nerve and muscle function as a result of mechanical stimulation. In particular, such components include electrodes for measuring the bulbocavernosus reflex. Such electrodes include a reference electrode and a pair of sensing electrodes. The reference electrode applies a small voltage (e.g., a range of 1.0 to 3.5 volts DC, but more preferably 1.25 volts DC) to the skin of a patient during, e.g., mechanical stimulation of the penis or clitoris, the pair of sensing electrodes is used to detect the actual bulbocavernosus muscle contraction or reflex due to the mechanical stimulation. In a first operation of the electrodes 2 and 4, the voltage applied by the reference electrode induces a small electrical current that is generally believed to be in a range of 5 microamperes to 9 microamperes, to flow through the patient's skin. This range in current is based on a presumed skin resistance of 1-10 meg-ohms, as well as the placement of the reference and sensing electrodes. In particular, in one preferred embodiment, the reference and sensing electrodes are pairwise separated by, e.g., ½ to 1½ inches (more preferably 1 inch) in an equilateral triangular pattern or another non-collinear arrangement. However, it is within the scope of the present disclosure that other voltages in addition to or alternatively to the 3.3 volts may be applied to the reference electrode. In particular, such reference voltages may be changed from one activation of the screening system and method to another activation.

In another embodiment of the operation of the electrodes 2 and 4, instead of the reference electrode 4 providing a current for flowing through the patient to the sensing electrodes 2, the reference electrode 4 is used to adjust the voltage potential of the patient. In one embodiment, the output from the DC voltage source 42 to the electrode 4 is adjusted to provide the reference electrode 4 with a voltage potential in a predetermined range such as ±1.25 volts. When the potential voltage at the reference electrode 4 is adjusted to such a predetermined range, the potential voltage of the patient (at least in the skin area of the muscle response being measured) will not vary substantially from this predetermined range. As one skilled in the art will understand, in order for the SEMG 35 to effectively determine voltage differences between the sensor electrodes 2, the voltages measured from the electrodes 2 must be within a predetermined range dependent on the particular electrical characteristics of the SEMG 35. Accordingly, since a patient may initially have an unacceptably wide range of voltage potentials (e.g., ±1,000 volts) due to, e.g., static electricity, and/or being in proximity to an electrical current generating source, this reference electrode voltage is determined by adjusting the electrical output of the DC voltage source 42 to insure the reference electrode 4 has a voltage within a predetermined range so that the voltages at the electrodes 2 can be expected to be within an acceptable range for the particular SEMG 35 being used. In one embodiment, the range of acceptable voltages to the SEMG 35 from the electrodes 2 is ±3.3 volts. In one embodiment, the sensing electrodes may be positioned on the patient's skin at the 9 O'clock and 3 O'clock position around the patient's rectum as shown in FIG. 2, wherein the sensing electrodes may be within, e.g., a range of one to two inches from the patient's rectum. Additionally, the reference electrode may be positioned on the patient's inner thigh, e.g., approximately four to eight inches from the patient's rectum.

In the first operation of the electrodes 2 and 4, the current induced to flow through the patient's skin (by activation of the reference electrode positioned as described above), in turn, causes a very small voltage potential to develop between the sensing electrodes. In the second operation the electrodes 2 and 4, a small electrical potential is generated by the muscle cells when these cells contract. Regardless of the which operation of the electrodes 2 and 4 is used, the small potential difference in voltage between the sensing electrodes is amplified to a usable level using an instrumentation amplifier, or an amplifier and a (high pass) filter combination. This circuit utilizes a standard surface EMG amplification circuit with a gain of 6174.72, and then summed (mixed) with some portion of the amplified potential difference between the sensing electrodes.

An embodiment of the screening system and method may also include one or more diagnostic computational models for receiving analytical information generated from the signals output by the sensing electrodes, and, e.g., an indication of patient symptoms for determining one or more likely patient diagnoses. In particular, such models may receive the following analytical information: no BCR response, a prolonged latency in BCR response, a prolonged BCR response, a temporal latency dispersion, an amplitude of the BCR, an integral of a graph of the BCR, etc.

Moreover, it is within the scope of the present disclosure that an embodiment of the screening system and method may be utilized for receiving and analyzing electrical signals indicative of reflexes from other patient bodily areas, such as the knee (patellar reflexes), and intravaginal stimulation.

Additional features and benefits of the present disclosure are disclosed in the accompanying figures and description hereinbelow. Such additional features and benefits, to the extent they are novel and non-obvious, are considered a proper subject matter for patent protection regardless of where their disclosure is provided in this Summary section.

BRIEF DESCRIPTION OF THE DRAWINGS

FIG. 1 shows the high level components of the novel apparatus for obtaining BCR measurements from electrodes (not shown) that are to be placed on a patient, wherein an exploded view of the probe 10 is shown.

DETAILED DESCRIPTION

Figure 1:
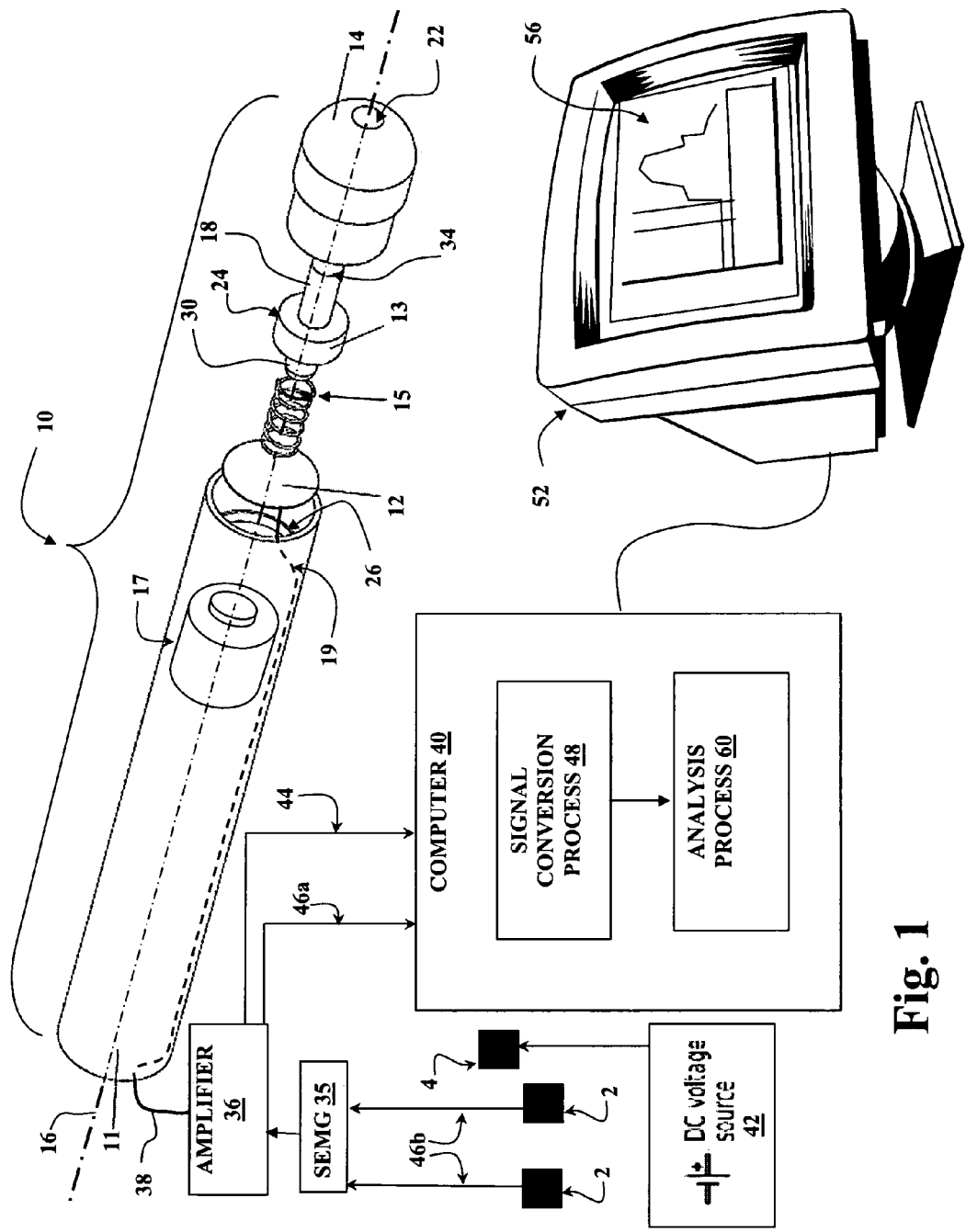
FIG. 1 shows an embodiment of the novel screening system and method disclosed herein. In particular.

The screening system and method disclosed herein includes mechanical stimulation of the penis or clitoris performed by a novel probe 10, wherein a first embodiment of this probe is shown in FIG. 1. In the embodiment of the probe 10 of FIG. 1 (shown in an exploded view), the probe includes a housing or handle 11, a piezoelectric disk or diaphragm 12, a stimulus plunger 13, a plunger housing 14, and a compression spring 15. When the probe 10 of FIG. 1 is assembled, the shaft 18 (of the stimulus plunger 13) extends through the bore or opening 22 of the plunger housing 14; however, since the expanded portion 24 of the stimulus plunger 13 can not fit through the opening 22, this prevents this plunger from sliding out the opening 22. The piezoelectric disk 12 seats against a stop 26 within the generally cylindrical interior of the housing 11. The compression spring 15 biases an opposing end 30 of the stimulus plunger 13 away from contact with the piezoelectric disk 12. The piezoelectric disk 12 is electrically activated by a power source that may be internal or external to the probe 10. FIG. 1 shows an embodiment of the probe 10 wherein there is a battery 17 within the housing 11 for energizing the disk 12 in a conventional manner as one of ordinary skill in the art will understand. Additionally, there is an electrical conductor 19 in the probe 10 between the disk 12 and an external electrical conductor 38, wherein signals indicative of the opposing end 30 contacting the disk are conducted by the conductors 19 and 38 for amplification and establishing a commencement of data capture from the electrodes 2 as will be described in further detail hereinbelow. Note that the use of a piezoelectric disk may be important to embodiments of the probe 10 over other mechanisms for detecting when to commence data capture from the electrodes 2 since a piezoelectric disc has a very quick response time that is required due to the very brief response times encountered by the BCR (e.g., generally less than 200 milliseconds).

At a very high level, the probe 10 is used to contact the patient's clitoris or penis and in particular, a probe tip 34

(referred to more generally hereinabove as a "patient contacting portion") contacts the patient's clitoris or penis for thereby inducing a patient reflex response. The detection of the probe tip 34 contacting the clitoris or penis is accomplished by the probe 10 outputting an electrical signal indicative of the stimulus plunger 13 contacting the piezoelectric disk 12. The BCR in response to such contact is then detected by electrical signals output from properly positioned electrodes 2 on the patient's skin. Subsequently, such signals are amplified and then analyzed for determining/identifying characteristics of the amplified signals (and/or a graph thereof), wherein such characteristics may be used for identifying patient ailments and/or providing a patient diagnosis.

The compression spring 15, and plunger housing 14 restrain the stimulus plunger 13 in such a way that it can only move along the axis 16, and in particular, towards the piezoelectric disk 12 when the stimulus plunger tip 34 comes in contact with another object (e.g., a patient) with sufficient force to overcome the opposing force of the compression spring 15. Accordingly, when the stimulus plunger tip 34 comes in contact with a patient with such force so that the stimulus plunger 13 comes in contact with the piezoelectric disk 12 (while the disk is electrically activated), the disk distorts its shape (e.g., bends), and the mechanical stress caused by the stimulus plunger 13 contacting the piezoelectric disk 12 causes an electrical charge to develop on the surface of the piezoelectric disk 12. Since the disk 12 is electrically connected to an amplifier 36 (via the connection 19 and the external conductor 38), the electrical charge induced on the disk is detected by the amplifier for amplification (and at least in some embodiments, filtered as well via a high pass filter). Thus, the disk 12 functions as a sensor for detecting contact between a patient and the tip 34. However, alternative sensors may be used to detect the transfer of pressure from the tip 34 to the disk 12. In particular, the opposing end 30 may include a pressure sensitive switch (not shown) for detecting contact with the disk 12.

In one preferred embodiment, the probe 10 may be handheld by an operator for placing the probe in contact with a patient's penis or clitoris for initiating bulbocavernosus reflex. Moreover, in one preferred embodiment, the contact of the probe tip 34 with the patient's clitoris or penis is performed by an abrupt, non-invasive, pressure inducing motion that is preferably somewhat unexpected by the patient. Such a motion may be similar to inducing patellar reflexes during an examination of a patient's knee reflexes.

A battery 17 (e.g., internal to the probe), or a transformer (e.g., external to the probe, and not shown) may be used to electrically activate the disk 12 for detecting contact by the end 30 when genital simulation is performed via contact with the tip 34 of the shaft 18 (which extends through the bore 22).

Although such piezoelectric disks 12 may generate mechanical or pressure vibrations (i.e., oscillations in directions coincident with axis 16, FIG. 1), when electrically activated, wherein such vibrations may be transmitted to the tip 34, in at least some embodiments of the probe 10, any such vibrations are of substantially no consequence in inducing the genital stimulation. Said another way, the piezoelectric disk 12 is used only as a sensor for detecting the movement of the tip 34 when it contacts the patient for genital stimulation. However, additional/alternative methods of inducing such a BCR is also within the scope of embodiments disclosed herein. For example, the probe tip 34 may be vibratory such that the tip may first come in contact with the patient's clitoris or penis, and then commences a vibratory motion, wherein at the commencement of the vibratory motion, the probe 10 may output a signal indicative of the commencement of the vibratory motion. In particular, such contact prior to the on set of the vibratory motion may be relatively gentle and non-abrupt. It is believed that such vibratory motion may be provided by a piezoelectric disk 12 of appropriate manufacture.

The amplifier 36 (e.g., an EMG amplifier and high pass filter) amplifies the detected charge on the disk 12 induced by genital stimulation. The amplifier 36 responds by outputting a corresponding amplified response signal on the transmission cable 44 for transmission to a computer 40. The computer 40 is programmed to receive the probe 10 amplified signal as input, and assuming an electrical potential is being concurrently applied to the reference electrode 4 (e.g., via the DC voltage source 42), the amplified probe signal on the cable 44 act as a trigger to activate a signal conversion process 48 for commencing to sample the amplified electrode 2 signals output by the amplifier 36 via the surface electromyography (SEMG) unit 35. The computer 40 then converts the amplified signals from the electrodes 2 into a time series of numbers representing the magnitudes of the samples. In particular, the amplified electrode signals output on connection 46a are amplifications of the differences of signals derived from the sensing electrodes 2 (FIGS. 1 & 2) on wires 46b. In particular, the SEMG 35 receives the voltage signals from both of the electrodes 2 and forms a difference signal that is output to the amplifier 36.

Figure 2:
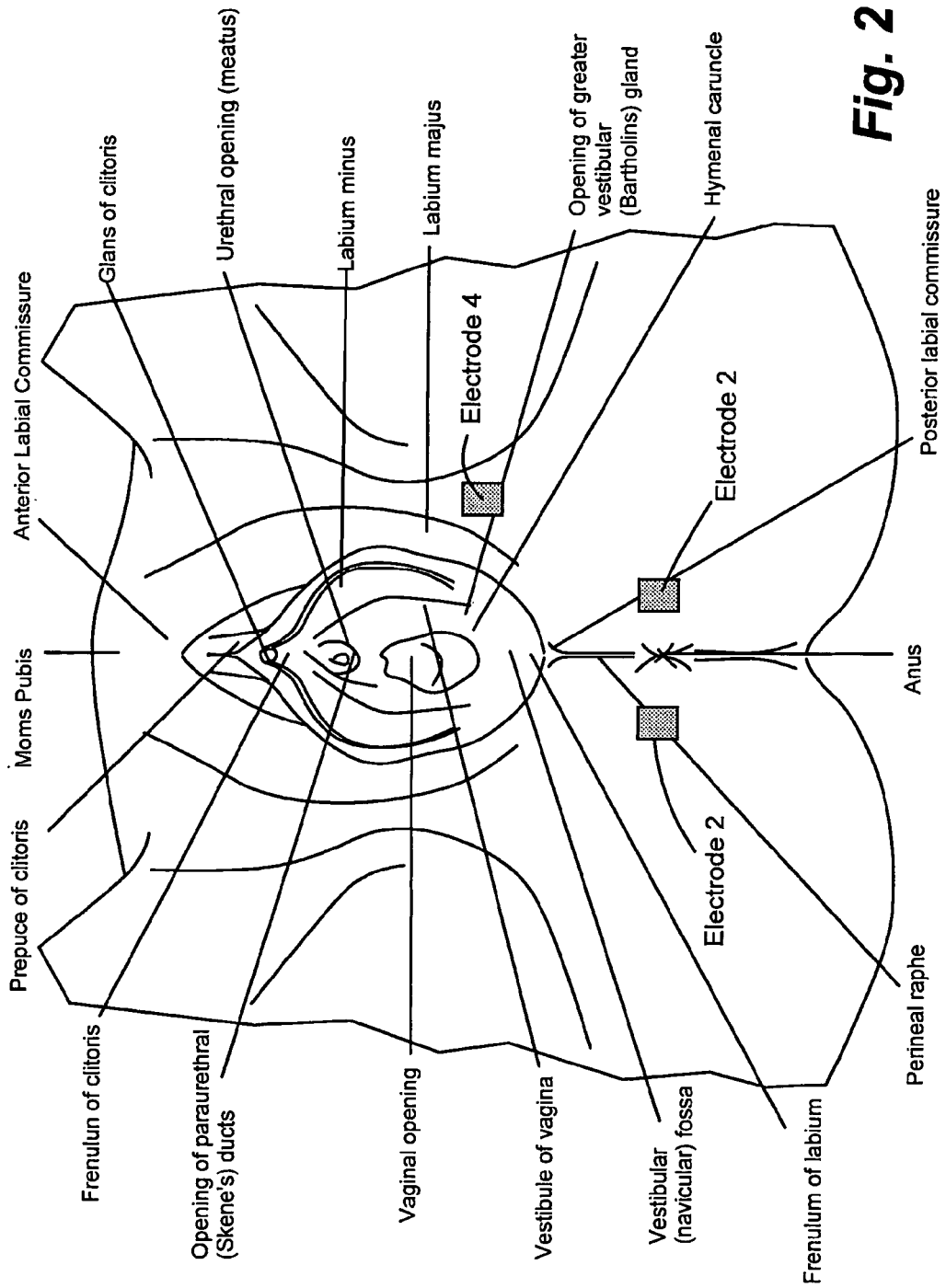
FIG. 2 shows one arrangement of the sensing electrodes 2 and the reference electrode 4 on a female patient for obtaining electrical signals for measuring BCR by the novel screening system and method disclosed herein.

As shown in FIG. 2, the sensing electrodes 2 may be placed at predetermined locations on a patient's body, e.g., at the 9 and 3 O'clock positions around a patient's rectum. Additionally, the reference electrode 4 may be positioned as also shown in FIG. 2 (e.g., in the patient's crotch area nearer to the genital area than the electrodes 2), or in some embodiments, the reference electrode 4 may be positioned on the patient's inner thigh (e.g., within six inches of the patient's genital area, and more preferably within 4 inches).

Note that the probe 10 (and in some embodiments, only the probe tip, as discussed in other sections hereinbelow) may be a single patient use device (i.e., non-reusable), e.g., the probe (or probe tip) is, in at least preferred embodiments, deactivated after it has been attached to the computer 40 for, e.g., an extended time period of such as 30 minutes. Such an extended time period gives an operator of the screening system and method ample time to obtain measurements of the bulbocavernosus reflex desired for the screening process. Note that when the probe 10 is battery powered such deactivation may be provided by a draining of the one or more batteries; e.g., once the probe is activated, current continues to flow from the one or more batteries until the batteries cannot power the probe. However, it is within the scope of the present disclosure that other methods of deactivating such batteries may be used, such as having an operator manipulate a deactivation switch that permanently disconnects the electrical power to the piezoelectric disk 12, or by providing an electronic timer in the probe 10 that activates with the first activation of the probe and deactivates the probe after a predetermined time has elapsed.

Amplified voltage signals derived from the difference of the signals output by the sensing electrodes 2 are provided to the computer 40, and in particularly, to the signal conversion process 48. The amplified voltage signals includes signals representative of the potential (voltage) differences between the sensing electrodes 2 as determined by the SEMG 35.

However, in an alternative embodiment, the wires 46b may connect directly to the amplifier 36 for simply amplifying and outputting each of its input electrode 2 signals. In such an embodiment, the signal conversion process 48 computes values representative of the potential differences between the sensing electrodes 2. Note that the SEMG 35 is not required in this embodiment.

Using the output from the amplifier 36, the signal conversion process 48 performs an analog to digital conversion, wherein the signals on the connection 46a are sampled, digitized, and then the digitized samples are input to a computational procedure for generating a time series of records (e.g., a series of measurement records) representing the magnitude of the amplified signals over a predetermined elapsed time. More specifically, for each sampling period, the connection 46a is sampled, the obtained sample is used to determine a number in a predetermined range of, e.g., 0 to 4096, wherein the greater the number, the greater BCR, and wherein such numbers from different reference electrode voltages can be reliably compared, summed, averaged or otherwise combined if desired. Moreover, the values in this predetermined range may be then normalized to the range 0.0 to 1.0, as one of ordinary skill in the art will understand.

However, it is within the scope of the present disclosure that, instead of the resulting time series of BCR numbers being monotonic with the BCR, such numbers may be inversely related to the BCR. Accordingly, instead of 1.0 being indicative of a maximal BCR response as is computed in the steps above, 0.0 would be indicative of the maximal BCR response.

The time period between samplings may be, e.g., 1.0 millisecond, although alternative time periods that are smaller or larger are within the scope of the present disclosure.

In one embodiment of the screening system and method, an analog to digital converter separate from the computer 40 may receive the signals from the amplifier 36 for performing the signal conversion process 48.

However, regardless of where the analog to digital conversion is performed, subsequently the analysis process 60 described hereinbelow is performed.

The analysis process 60 may be instrumental in determining BCR patient data to be output to the display device 52 (FIG. 1), to a database (not shown), and/or to a report generator (not shown). In particular, the analysis process 60 may determine one or more of the following BCR related measures when provided with digital data output from the signal conversion process 48:
 (a) a latency between the detection of the response signal on cable 44, and commencement of the BCR signals from the electrodes 2,
 (b) a duration of the BCR signals from the electrodes 2,
 (c) a value indicative of a magnitude or strength of the BCR, and/or
 (d) an attenuation in the magnitude or strength of the BCR (e.g., in comparison to an expected magnitude or strength).

Additionally, as described hereinbelow, the analysis process 60 may also determine associations between, e.g., values such as (a) through (d) immediately above, and likely a diagnosis of a patient's symptoms.

In order to more fully describe the processing and output of the analysis process 60, a description of a representative embodiment of output 56 (FIG. 1, and more particularly FIG. 5) from the analysis process is now described, wherein this output 56 is provided to a computer display device 52 operatively connected to the computer 40. In particular, referring to FIG. 5, a graph 62 may be displayed, wherein the horizontal (X) axis is elapsed time (in milliseconds), and the vertical axis represents signal magnitude values (preferably normalized to the range 0.0 to 1.0). A time value identified by the vertical line 64 on the graph 62 represents the detected application of the patient stimulus from the probe 10 as determined from the response signal on the cable 44. A subsequent time is identified by the vertical line 66 which represents the initial onset of the BCR in response to this stimulus. The Y (vertical) axis of the graph 62 represents the magnitude of a detected muscle (BCR) contractions. This magnitude is normalized in the range of 0.0 to 1.0 with 1.0 being the highest magnitude. The time series of normalized BCR response numbers is represented by the graphical signature 68. The horizontal line 72 is a reference line to facilitate viewing the graph 62. The auxiliary trace 74 is also for operator reference as well. In particular, the trace 74 provides the operator with a visual indication of all changes in voltage signals received from the electrodes 2 and the probe signals received on cable 44, wherein each change is shown by an upward movement in the trace 74. The values of the trace 74 may be computed as follows: $Y_n = X_n \cdot G$ where $G = 1/4096$, and $X_n$ is the $n^{th}$ BCR response value, and $Y_n$ is the normalized representation of the incoming time series, $X_n$ is the input signal, G is the constant and n is the time start to stop.

In one embodiment, the position of the line 66 is manually assigned by an operator, wherein, e.g., the operator is able to set (and/or select and drag) this line to the position the operator determines is most indicative the onset of the BCR. However, in an alternative embodiment, the position of the line 66 may be estimated by the screening system and method, e.g., by identifying an initial time where the graphical signature 68 remains above a predetermined threshold for a predetermined elapsed time.

A patient symptom can be entered in the interaction box 76, and the collected patient data, and/or measurements/characteristics derived therefrom, can be associated with this symptom. Accordingly, once an actual diagnosis of the cause of the symptom is determined for each of a plurality of patients, associations may be obtained between: (i) such actual diagnoses, and (ii) the symptoms and corresponding measurements/characteristics of the collected patient data (e.g., patient graphical signatures 68). In particular, such associations may become the basis for one or more predictive models for predicting a likely (if any) patient abnormality/diagnosis, wherein such associations may be formed by one or more of: a statistical method (e.g., a regression technique), a learning system (e.g., a vector machine, and an artificial neural network), and/or a pattern matching system (e.g., a fuzzy logic system, etc.). In particular, it is believed that such associations may be based substantially on the symptom identification together with one or more of the following BCR measurements:
 (a) a latency between the graphical signature 68 (equivalently, the BCR signals from the electrodes 2), and the detection of the response signal on cable 44,
 (b) a duration of the graphical signature 68 (equivalently, the BCR signals from the electrodes 2),
 (c) a magnitude of the graphical signature 68 (equivalently, the BCR signals from the electrodes 2),
 (d) an attenuation in the magnitude of the graphical signature 68 (equivalently, the BCR signals from the electrodes 2), wherein such attenuation is, e.g., in comparison to an expected magnitude, and/or
 (e) no detectable graphical signature 68 (equivalently, the BCR signals from the electrodes 2).

Alternatively/additionally, the resulting time series of the digital data stream from the signal conversion process 48 can be input to an embodiment of analysis process 60 for hypothesizing a diagnosis for (any) one or more of sexual, lower spinal, and/or urological dysfunctions. Such hypotheses may be generated by one or more hypothesis generating predictive models which are described hereinbelow.

Of course, if none of the models identify a likely diagnosis, then it may concluded that the patient is not likely to have dysfunctions, such as sacral cord lesions, or prudential neuropathy (impotence, chronic back pain, fecal incontinence), resulting from lack of sacral plexus integrity.

Figure 5:
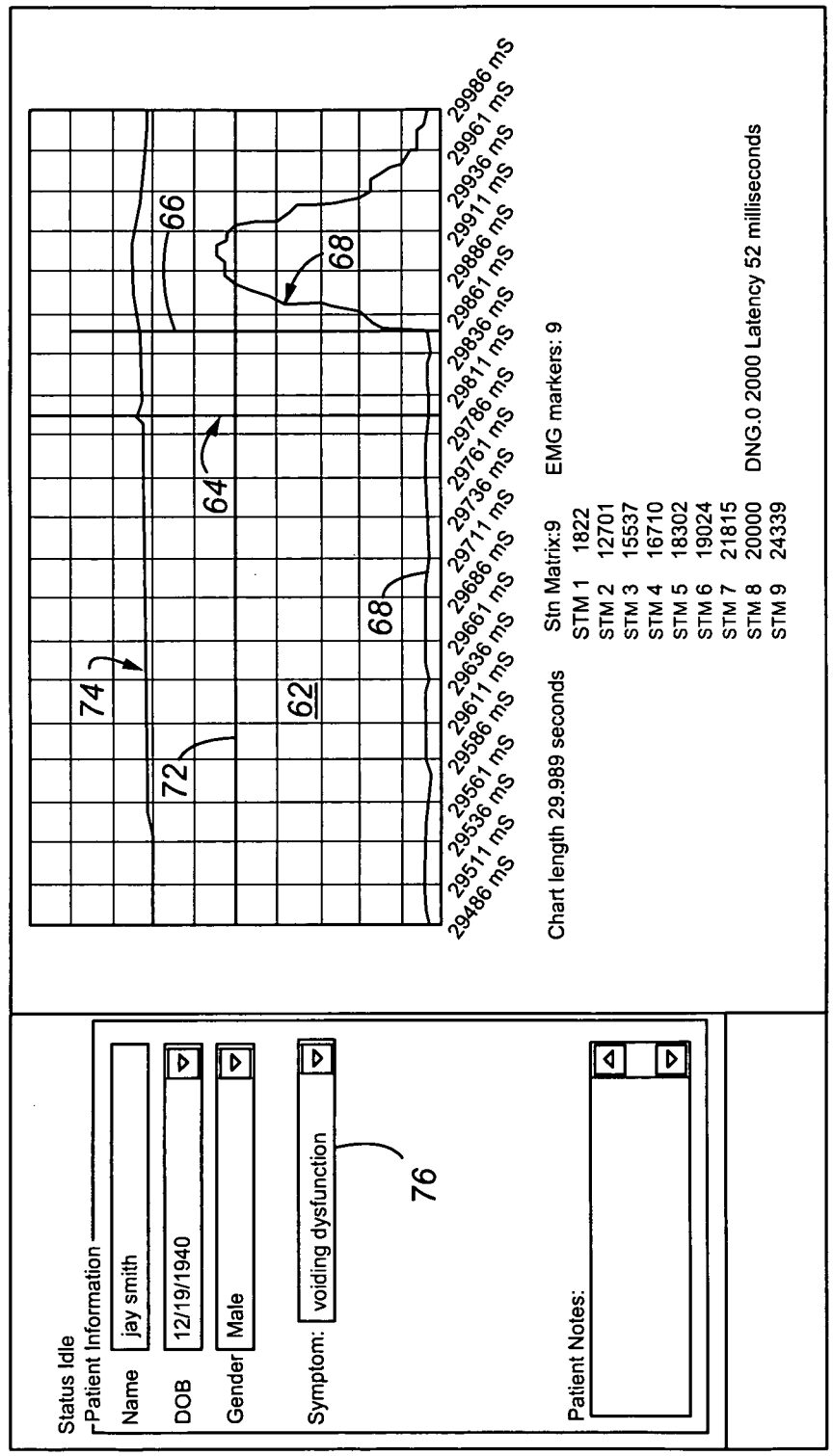
FIG. 5 shows an output screen for viewing BCR measurements, in particular, the following are shown: the magnitude and location of the applied stimulus (via the probe 10), the magnitude and time for a time series of responses to the stimulus, the time delay between the application of the stimulus and corresponding response(s).

In one such predictive model, a prolonged bulbocavernosus reflex of more than 45 msec., such as is shown in FIG. 5, may be considered indicative of a neurological disorder. More precisely, such a model may hypothesize one of the following disorders: sacral cord lesions, prudendal neuropathy (impotence, chronic back pain or disc disease), and lesions of the cauda equine. In one embodiment, prolonged such bulbocavernosus reflexes are determined by a calibration or training process, wherein time series BCR data is obtained from patients with such neurological disorders, and such data is used for determining parameters indicative of such disorders.

Additionally, such a model (or another model) may also identify an abnormal BCR latency, wherein such latency (e.g., in a range of 50+ msec.) may be indicative of the following disorders: diabetic neuropathy, or other, neurogenic disease process.

Moreover, such a model (or another model) may also provide output corresponding to an indication of a substantial absence or attenuation of the BCR within the predetermined sample time period for sampling the signals from the electrodes 2. In particular, such BCR absence or attenuation may be indicative of the following symptoms: sexual dysfunction, voiding dysfunction, and bowel dysfunction. Accordingly, the following may be considered likely diagnoses: decreased or absent sacral plexis response. Note that attenuation of the BCR in a graphical signature 68 also may be quantified as no bulbocavernosus response, particularly if such attenuation is below, e.g., a predetermined threshold such as a threshold corresponding to 2 micro volts above a baseline output from the muscle(s) at rest.

There are numerous measurements related to the graph 62 that may be determined to be effective for predicting patient disorders (i.e., diagnosing a patient's symptom(s)), and various calibration or training processes may be used to determine the measurements that are most effective in providing an appropriate diagnosis. In addition to the measurements/characteristics of the BCR patient data received from the signal conversion process 48, some additional measurements that may be useful in diagnosing a patient's symptoms are: the integral of the graphical signature 68, the number or magnitude of local minima or maxima, an extent of the graphical signature 68 below/above a predetermined value, etc.

In one embodiment of the presently disclosed system and method for screening, instead of (or in addition to) hypothesizing/diagnosing various disorders/symptoms, any of the above mentioned statistics or characteristics of the graphical signature 68 may be computed from the BCR digital data streams, and then output to a technician, nurse or physician for review and interpretation.

In one embodiment of the screening system and method, one or more of the following assessments may be obtained from analysis of the BCR time series measurements generated by the signal conversion process 48:

(a) the patient's spinal cord segments S2 through S4 are in tact,
(b) there may be lesions in the cauda equine,
(c) an indication of actual chronic back pain, e.g., as asserted by the patient,
(d) the latency between genital stimulation and the resulting bulbocavernosus reflexes are within a normal range and are not indicative of neurological order (e.g., contrary to what is asserted by the patient),
(e) the latency between genital stimulation and the resulting bulbocavernosus reflexes are abnormal and are indicative of neurological order,
(f) the BCR time series measurement are indicative of a voiding dysfunction, bowel dysfunction, and/or
(g) the time series measurements are indicative of a male impotence condition.

A report may be generated by the analysis process 60, and the report can be printed for entry into the patient's medical records, wherein the report may include any of the information disclosed hereinabove.

Figure 3:
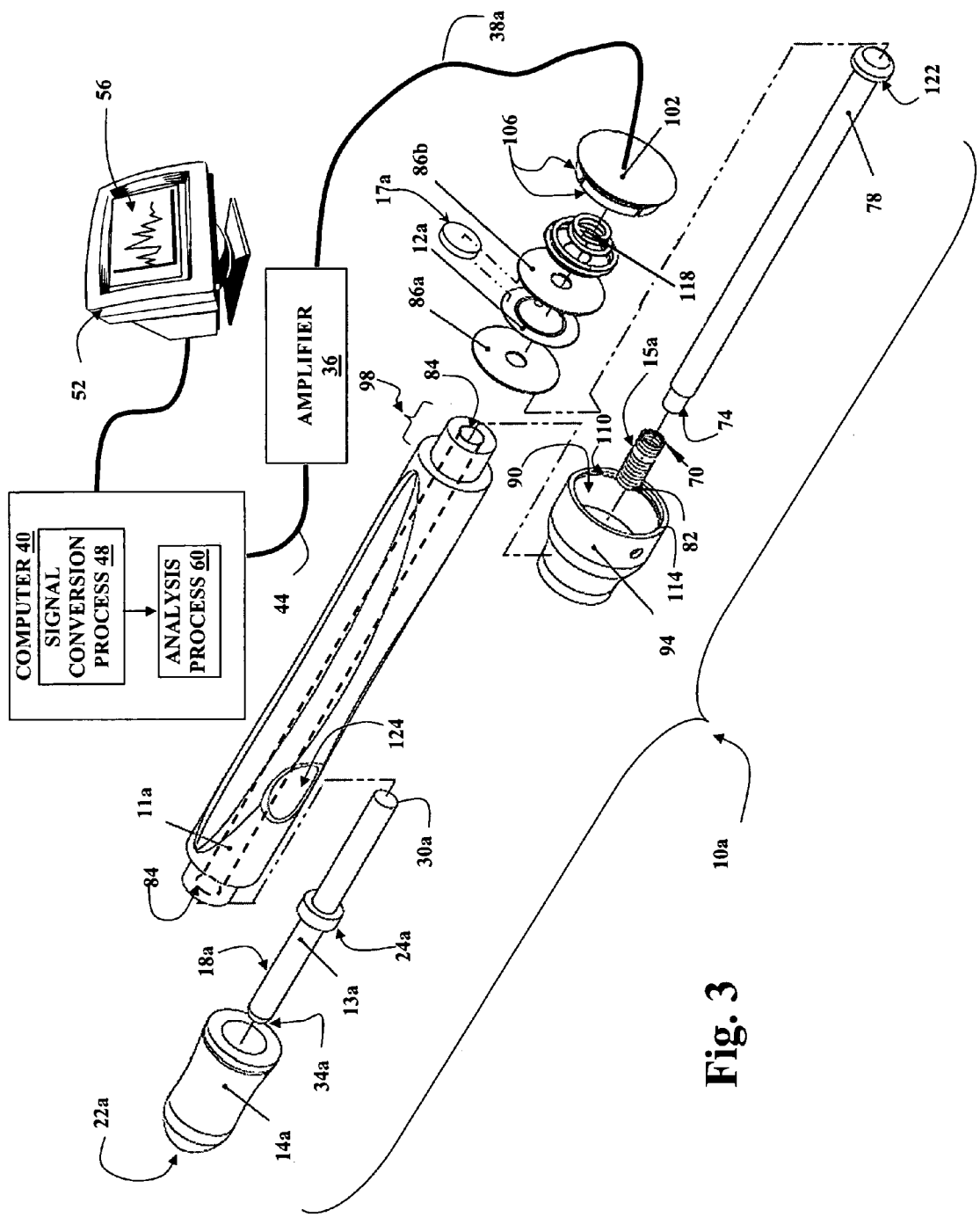
FIG. 3 shows the components of another embodiment of the novel screening system and method, wherein an exploded view of the probe 10a is shown.
Figure 4:
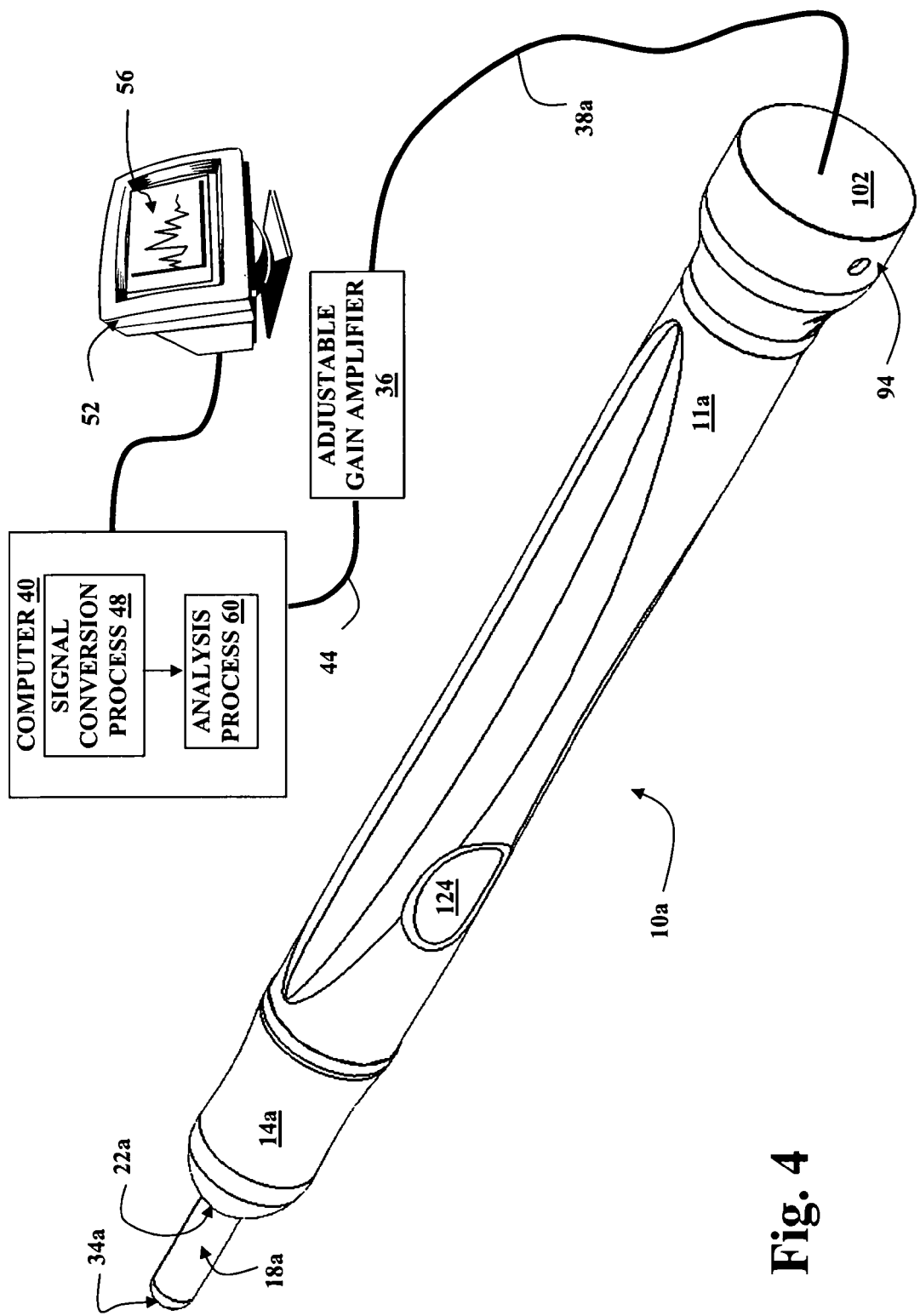
FIG. 4 shows the embodiment of FIG. 3 with the probe 10a fully assembled.

Another embodiment of the probe is shown in FIGS. 3 and 4, wherein components that functionally correspond to components of probe 10 described hereinabove are identified by the same numerical label except with an "a" following. Accordingly, the probe is identified by the label "10*a*".

One or more of FIGS. 3 and 4 show:

(i) a handle 11*a* for holding the probe 10*a*,
(ii) a piezoelectric disk 12*a* for at least detecting a mechanical pressure from the tip 34*a* for stimulating a patient's penis or clitoris in a similar manner as discussed hereinabove.
(iii) a stimulus plunger 13*a* for transferring toward the piezoelectric disk 12*a* a resulting mechanical movement of the tip 34*a* contacting the patient's penis or clitoris; in particular, the plunger 13*a* includes the tip 34*a*, and an opposing end 30*a*,
(iv) a plunger housing 14*a* which is operatively attached to an end of the handle 11*a* for retaining at least part of the stimulus plunger 13*a* therein; note that as with the plunger housing 14 of the probe 10, the plunger housing 14*a* includes an opening or bore 22*a* through which the shaft 18*a* of the stimulus plunger 13*a* extends, and the stimulus plunger 13*a* (as with the stimulus plunger 13) includes an expanded portion 24*a* that prevents the plunger from slipping entirely through the opening 22*a*,
(v) a compression spring 15*a* for separating the stimulus plunger 13*a* from the piezoelectric disk 12*a*; in particular, the end 70 of the spring 15*a* fits onto an end 74 of the pressure transfer rod 78, and the spring end 82 contacts the opposing end 30*a* of the plunger 13*a* within the channel 84 extending the length of the handle 11*a*.

When the probe 10*a* is fully assembled, the piezoelectric disk 12*a* is sandwiched between washers 86*a,b* (preferably plastic). The disk 12*a* and washers 86 are contained within an interior 90 of the piezohousing 94 which is secured to the end 98 of the handle 11*a* by, e.g., adhesive, mating threads, a snap fit, or another comparable securing mechanism. An endcap 102 seals the disk 12*a* and the washers 86*a* and 86*b* within the interior 90 by, e.g., snapping the semi-annular locking projections 106 onto the ridge or recess 110 adjacent the opening 114 of the interior 90. Additionally retained in the interior 90 is a tapered compression spring 118 which provides a pressure on the piezoelectric disk 12*a* at all times. When the pressure transfer rod 78 is positioned in the channel 84, the expanded head 122 rests against the center opening in the washer 86*a*, but the expanded head is too large to fit through this opening.

During operation of the probe 10*a*, an operator activates the probe 10*a* by, e.g., a quick downward (preferably at least somewhat unanticipated) pressure of the stimulus tip 34*a* on the clitoris or penis. In one embodiment, when electrical power is already being supplied to the disk 12*a* from an electrical power source, e.g., a battery 17a (preferably positioned between the disk 12a and the washer 86b) within the handle 11a, or an exterior electrical power supply (not shown), such activation of the probe by contacting a patient's genital area causes the end 74 of the transfer rod 78 and the opposing end 30a to come in contact (or otherwise become configured for the transfer of tip 34a movement). Accordingly, the movement of the tip 34a toward the interior of the plunger housing 14a causes movement of the transfer rod 78 for increasing pressure on the disk 12a, wherein such increased pressure results in an additional electrical charge to develop on the surface of the piezoelectric disk. Since the disk 12a is electrically connected to the amplifier 36 (via a connection not shown, and the external conductor 38a), the electrical charge induced on the disk is detected by the amplifier for amplification. Thus, the disk 12a functions as a sensor for detecting contact between a patient and the tip 34a. However, note that alternative embodiments of sensors may be used to detect the transfer of pressure from the tip 34a to the disk 12a. In particular, the opposing end 30a may include a pressure sensitive switch (not shown) for detecting contact with the disk 12a.

Alternatively, such activation of the probe 10a by contacting a patient's genital area may initiate an electrical current from a power source (e.g., a battery 17a, or an exterior electrical power supply) to the piezoelectric disk 12a thereby causing the disk to apply vibratory pressure to the transfer rod 78 for initiation of the BCR reflex. Thus, when the tip 34a is pressed against the penis or clitoris, the shaft 18a slides further into the plunger housing 14a and handle 11a for thereby compressing the spring 15a so that vibratory pressure from the disk 12a results in mechanical vibrations being transferred to the tip 34a (via the shaft 18a and the transfer rod 78) for stimulation of the penis or clitoris.

As with the probe 10, at the time that the vibratory pressure commences to transfer to the tip 34a, a mechanical stress caused by the head 122 applying additional pressure against the disk 12a causes an electrical charge to develop on the surface of the disk. This electrical charge is communicated to the external conductor 38a via an internal conductor (not shown), and subsequently conveyed to the amplifier 36 (e.g., an EMG amplifier) where it is detected, and amplified as described hereinabove. The amplified signal is transmitted to the computer 40 (via transmission cable 44) as also described hereinabove.

Accordingly, the probe (10 or 10a) at least provides electrical signals for identifying when to commence measuring an electrical response (via the sensing electrodes 2) to a BCR.

In each of the above embodiments of the probe 10 and 10a, the included disk (or other vibration generating element) may be selected for generating vibrations having frequencies in the range of 2 Hz to 20 Hz, and more preferably in the range of 4 Hz to 10 Hz, most preferably approximately 5 Hz. In particular, the inventors have determined that vibrations outside of these ranges have reduced effect on the patient, and/or may be painful.

Note that in addition to activation of the probe (10 or 10a) by contacting a patient's genital area, the probe may include an activation switch (e.g., button switch 124, FIG. 3), wherein pressing (or otherwise manipulating) such a switch induces a current to flow to the disk 12a for providing an electrical potential to the disk. Such a switch may only activate the electrical features of the probe, and not be capable of turning off such features. Accordingly, as described hereinabove, a battery powered embodiment of the probe may be used for only a prescribed time before becoming non-functional due to, e.g., one or more dead batteries. However, other mechanisms may also be used for prohibiting the reuse of the probe with another patient. For example, a deactivation timer may be incorporated into the probe.

Note that for embodiments of the probe wherein the included disk remains in a vibratory active state once the probe is powered on, such vibrations (or lack thereof) can be an indicator to an operator as to whether the probe has been previously used. For example, if upon activation of the activation switch, the operator senses no vibratory response from the disk 12 or 12a (e.g., due to a dead battery, and/or due to detection that the activation switch has been previously used to power the probe, etc.), then the operator will be alerted that the probe is at least non-functional and may have been used previously.

Moreover, at least some embodiments, the probe (10 or 10a) may include a light emitting diode to notify an operator that the probe has not been previously used. For example, for a functional probe that had not been previously activated, such a diode would be activated when the button switch 124 is pressed for electrically activating the probe, and such a diode would emit light until a predetermined probe state occurs that deactivates the probe and prevents the probe from being reactivated.

Embodiments of the probe (10 or 10a) may also prohibit their reuse based not only on an elapsed time, but also on the number of times the probe tip is depressed toward the interior of the probe housing. For example, by providing no more than, e.g., five probe tip depression within a predetermined maximal elapsed time of probe activation, additional assurance that the probe will not be reused with another patient can be provided.

Figure 6:
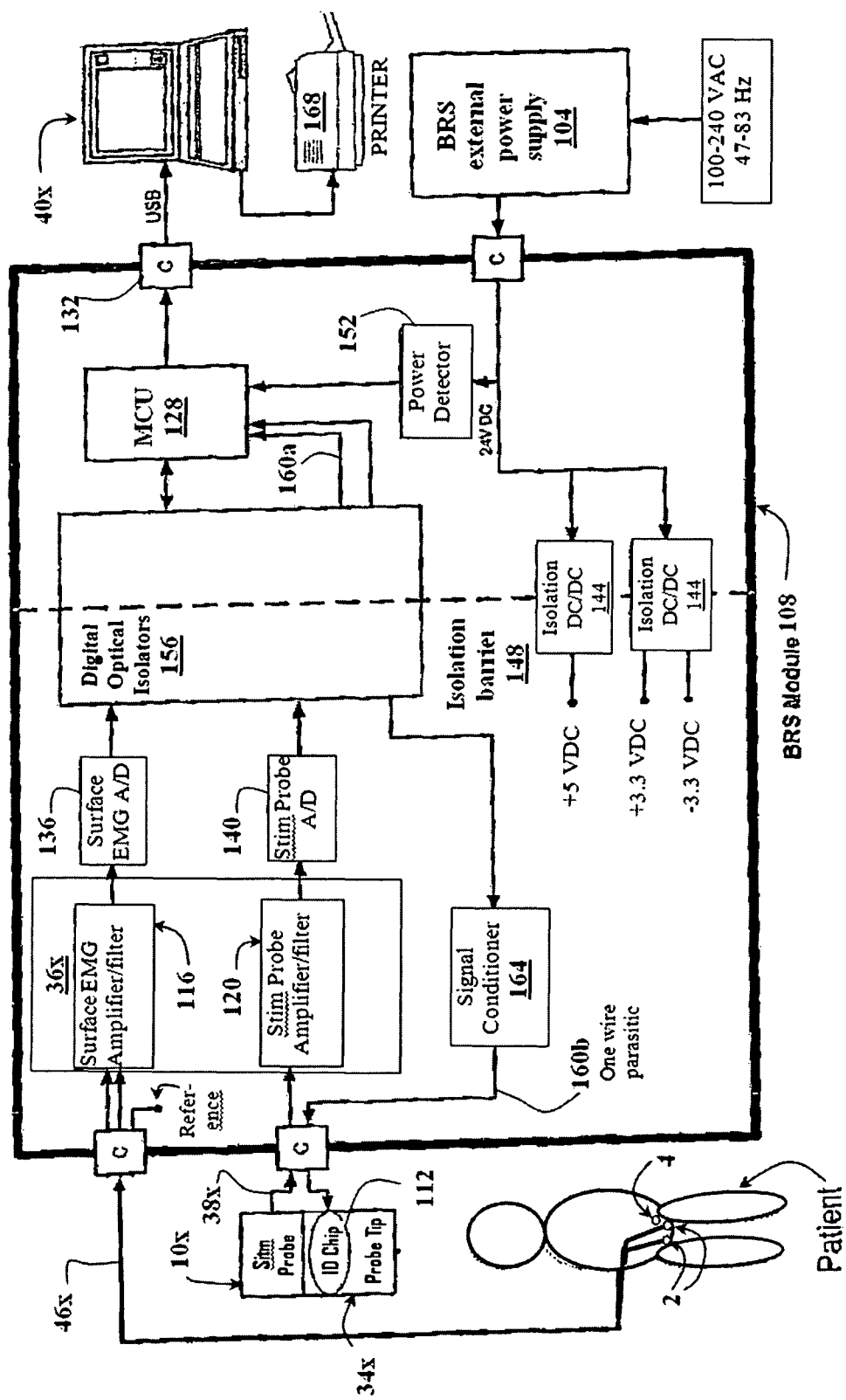
FIG. 6 shows a block diagram of another embodiment of the screening system and method disclosed herein.

Referring now to FIG. 6, a more detailed diagram of an embodiment of the screening system and method is disclosed. The components (and communications therefor) described in FIG. 6 that have substantially identical functionality with components described hereinabove are identified by the number of the component described above followed by "x". Moreover, an embodiment of the probe 10x shown in FIG. 6 may be one of: probe 10 or 10a, or another embodiment. The components, communications, and data processing of the embodiment of FIG. 6 are described in the following sections (1) through (7).

(1) Description of the Components Shown in the Embodiment of FIG. 6.

(1-1) A Bulbocavernosus Reflex Stimulation (BRS) External Power Supply 104 is a medical grade power supply that is used to supply 24 volt DC power to the BRS Module 108 (described hereinbelow).

(1-2) A probe 10x is used to administer and measure the genital stimulation in a manner as described in previous embodiments hereinabove. The tip 34x in the probe 10x may be replaceable and may contain an ID chip 112. The ID chip 112 is used to prevent its tip 34x from being used more than once (e.g., prevented from being used on more than one patient) as is described further hereinbelow. Thus, instead of the entire probe 10x being non-reuseable on different patients, only the probe tip 34x is non-reuseable. The probe 10x interfaces to the BRS Module 108 (which includes an amplifier/filter 36x having substantially identical function to the combination of the SEMG 35 and the amplifier 36 disclosed in FIG. 1 and described hereinabove). In particular, the amplifier/filter 36x includes a surface EMG amplifier/filter 116 for receiving signals from the electrodes 2, and a stim(ulus) probe amplifier 120 for receiving signals indicative of probe 10x activation (via cable 38x. Both amplifiers 116 and 120 are described hereinbelow.

(1-3) The ID chip 112 provided in the probe tip 34*x* can output data to the BRS module 108 for determining whether the probe tip has been previously used to contact a patient, and if so, the elapsed time since this first use. In one embodiment, such data includes a time and date that the probe 10*x* was first activated, or if not previously used such data may include a predetermined value such as zero. Thus, the ID chip 112 includes a non-volatile data storage for storing data indicative of the probe tip's activation history (which may be only the initial date and time of, if any, the probe tip's first activation). In one embodiment, such activation history may include the time and date of each activation, and/or the elapsed time of each activation. Note that the ID chip 112 may be activated each time the probe 10*x* is operably connected to the BRS module 108. In particular, data is communicated on the conductors 160*a* and 160*b* from the MCU 128 processor (described below) for activating the ID chip 112 so that it will respond to the MCU with an acknowledgement of whether the probe tip 34*x* can or cannot be used for a subsequent patient contact. Accordingly, an acknowledge by the ID chip 112 that the probe tip 34*x* cannot be used will cause the MCU 128 to issue commands to at least prevent data collection from the probe 10*x*, and preferably provide an indication to the operator that the probe having this tip cannot be used for such data collection. There are various ways to provide such an indication of probe non-use, e.g., visual display on the BRS module 108 may be used such as a red LCD may light when the probe cannot be used, and a green LCK may light when the probe can be used. Alternative/additional visual and/or auditory presentations are also within the scope of the present disclosure. Accordingly, iconic and/or textual information can be visually presented to an operator for indicating whether the probe 34*x* (with its current probe tip 34*x*) can be operably used. Alternatively/optionally, synthetic speech or various sounds may be used for indicating whether the probe 34*x* (with its current probe tip 34*x*) can be operably employed.

(1-4) The BRS Module 108 is the interface unit between the BRS Computer 40*x* and both the patient applied probe 10*x* and EMG leads (collectively labeled as 46*x* in FIG. 6). Subsystems/components of the BRS Module are as follows:

(1-4.1) Micro Controller Unit (MCU) 128.
  The MCU 128 is a microprocessor that controls and monitors data and communication in the BRS Module 108. The MCU 128 contains firmware for the following functions:
  a. Connects and communicates with the BRS computer 40*x* via the USB interface 132.
  b. Upon command the MCU 128, collects digital data from the surface EMG analog to digit converter 136 (which converts the amplified voltage differences from the electrodes 2 to digital data), and the Stim Probe analog to digital converter 140 (which converts the amplified probe activation signal to digital data). The MCU 128 then sends such digital data to the BRS computer 40*x* via the USB interface 132,
  c. Monitors the 24 volt power supply 104 and communicates the status of this power supply to the BRS computer 40*x* via the USB interface 132.
  d. Reads and updates the IC chip 112 in the Stim Probe Tip 34*x* to ensure that the Probe Tip is not used for more than 30 minutes.

(1-4.2) Isolation DC/DC Converters 144.
  The Isolation DC/DC converters 144 supply isolated −3.3V, +3.3V, and 5V DC power to the patient connected components; in one embodiment such converters may be: a Datel UWR-5/2000-D24E-C Murata NDTD0503C or similar components as one of ordinary skill in the will understand.

(1-4.3) Isolation Barrier 148.
  The Isolation Barrier 148 provides the necessary creepage and clearance distances between the AC mains connected power and patient connected power.

(1-4.4) Power Detector 152.
  The power detector 152 is used by the microprocessor MCU 128 to monitor the state of the 24 Volt Power supply from the power supply 104.

(1-4.5) Digital Optical Isolators 156.
  The Digital Optical Isolators 156 are used to provide isolation between the patient connected electronics (i.e., the electrodes 2 and 4), and USB powered electronics (i.e., the computer 40*x*). The optical isolators 156 allow the MCU 128 to communicate with the analog to digital converters 136 and 140, and the chip 112 in the Stim Probe Tip 34*x* via a one wire interface provided by the conductors 160*a* and 160*b*.

(1-4.6) Stim Probe Amplifier/Filter 120.
  The Stim Probe Amplifier/Filter 120 amplifies and filters the signal from the Stim Probe 10*x* to a level that can be read by the A/D converter 140. The MCU 128 controls the analog to digital conversion process of the A/D converter 140.

(1-4.7) Stim Probe A/D (Analog to Digital) Converter 140.
  The A/D converter 140 is an analog to digital converter for changing the incoming amplified Stim Probe 10*x* signal into a digital value for the MCU 128 to read and then send to the computer 40*x* for analysis. The MCU 128 controls the A/D conversion process of the A/D converter 140.

(1-4.8) Surface EMG Amplifier/Filter 116.
  The Surface EMG Amplifier/Filter 116 amplifies and filters the voltage signals from the electrodes 2 to a level that can be read by the A/D converter 136.

(1-4.9) Surface EMG A/D (Analog to Digital) Converter 136.
  The converter 136 is an analog to digital converter for changing the incoming amplified Surface EMG signal into a digital value for the MCU 128 to read and send to the computer 40*x* for analysis.

(1-4.10) Signal Conditioner 164.
  The signal conditioner 164 translates the two wire interface 160*a* from the MCU 128 to/from the 1 wire interface 160*b* which communicates with the ID chip 112.

(1-5) Computer 40*x*.
  The computer 40*x* provides a user interface for displaying, e.g., displays such as shown in FIG. 5 described hereinabove. The computer 40*x* communicates with the BRS Module 108 through the USB interface 132. The computer 40*x* contains a custom application for at least the following functions:
  a. Communicates and receives status information from the BRS Module 108 regarding power on (more generally activation status), information for obtaining probe tip ID chip 112 information (e.g., BCR time series values, ID chip status, etc).

b. Sends commands to the BRS Module 108 to acquire data from the Stim probe 10x.
c. Graphs and/or analyses data from the Surface EMG data channel (which includes the components 116, 136, 156, and 128), and from the Stim Probe data channel (which includes the components 10x, 38x, 120, 140, 156, and 128) for presentation to an operator. The graphs and/or analysis performed may be as described hereinabove regarding the analysis process 60 (FIG. 1) and the user interface of FIG. 5.
d. Processes the Stim probe 10x signal to determine the time of commencement of patient stimulation.
e. Allows an operator to input patient and physician information.
f. Stores test case data for later review and analysis.
g. Prints reports is instructed by an operator.

(1-6) Printer 168.
The printer 168 is used by the Computer 40x to print reports on patient cases.

(2) High Level Processing of Data in the BRS Module 108.
For each of the EMG data channel (which includes the components 116, 136, 156, and 128), and the Stim Probe data channel (which includes the components 10x, 38x, 120, 140, 156, and 128) the high level algorithm used to process incoming analog data can be simplified down to:
(a) first inputting the analog data to an amplifier and a high pass filter (provided by the components 116 and 120), followed by a RMS detector process (provided by the A/D converters 136 and 140), and
(b) providing the output from (a) immediately above to a process (provided by the computer 40x), wherein the data is decimated down from a 2 KHz sample rate to a 1 KHz sample rate by simply saving every other sample.

The signal provided by each of the above-identified channels passes through its own filter and RMS detector and decimator before being stored in the computer 40x (or a database operably connected thereto).

(2-1) Implementation.
Each high pass filter is implemented as a 4 pole Butterworth filter having a cutoff frequency of 10 Hz and a pass band ripple of 0%. Each RMS detector is implemented using the Root Mean Square algorithm for a finite number of sequential samples.

(3) Filter Algorithm
Each filter used in the amplifier/filter 36x may be a Chebyshev filter optimized for a pass band ripple of 0%, otherwise known as a Butterworth filter. Each of the filter is a form of recursive filter, which is also called an IIR (Infinite Impulse Response) filter. For a detailed description of recursive filters and the implementation see the Scientists and Engineers Guide to Digital Signal Processing chapters 19 and 20, by Steven W. Smith, published by California Technical Publishing.

(3-1) Implementation.
Each of the filters utilizes an embodiment of the following equation, as one of ordinary skill in the art will understand.

$$y[n]=a_0x[n]+a_1x[n-1]+a_2x[n-2]+a_3x[n-3]+\ldots+a_nx[0]+b_1x[n-1]+b_2x[n-2]+b_3x[n-3]+\ldots+b_rx[0],$$

wherein for $0 \leq i \leq n$, $a_i$ is the recursion coefficient of the incoming signal, $b_i$ is the recursion coefficient of previous output signals, $x[i]$ is the incoming signal, and $y[i]$ is the output signal.

(4) RMS Algorithm

The RMS (Root Mean Square) is a measure of the magnitude of a varying quantity (e.g., a signal), which is calculated for a series of discrete values for a continuously varying function. The BRS software uses the RMS algorithm to transform the incoming signals into a magnitude (as opposed to a wave) so that the analysis by an operator easier. The period of the function is configurable by the operator. For a more detailed description of the RMS algorithm see http://en.wikipedia,org/wiki/Root_mean square.

(5) Stimulation Marker Detector Algorithm.
The Stimulation Marker Detector algorithm scans the stimulation probe time series (received via the cable 38x) looking for a change in signal amplitude of 1%±0.1% within a 50-millisecond window. If/when a change in amplitude at t+50 that exceeds this threshold is detected, a marker is placed in the data stream of the Stim Probe data channel, wherein the marker corresponds to time t. If a marker is detected, this algorithm is blacked out for a period of 1.5 seconds.

(5-1) Implementation
For each sample in the time-record (minus 50 mS) perform the following steps:
(5-1.1) Scan ahead of current position up to 50 mS;
(5-1.2) If the magnitude of the stimulus signal meets criteria, place a marker in the data stream of the Stim Probe data channel;
(5-1.3) Black out additional marker placement for 1.5 seconds From the disclosure hereinabove, and the accompanying figures, it is believed that one of ordinary skill could manufacture the present screening system, and in particular, the probe (10 and/or 10a). More particularly, FIGS. 1 and 3 are believed to provide effective indications as to how the components of the embodiments of the probe would be assembled.

The novel system and method disclosed herein is valuable in evaluation of urinary disorders in adults and children, as well as erectile dysfunction when neurological etiology is suspected. While various embodiments of the present disclosure have been described in detail, it will be apparent that further modifications and adaptations of the embodiment disclosed herein will occur to those skilled in the art. It is to be expressly understood that such modifications and adaptations are within the spirit and scope of the present disclosure.

What is claimed is:

1. A non-surgically implantable method for measuring a bulbocavernosus reflex, comprising:
a probe a patient contacting portion configured for being brought into contact with a predetermined body area of a patient with sufficient force for inducing, via a mechanical stimulation of the predetermined body area from the force, a reflex of bulbocavernosus muscle, said probe comprising;
(i) a housing with a bore there through, said housing containing a piezoelectric disk, said disk electrically connected to an amplifier and activated by a power source;
(iii) a patient contacting portion comprises stimulus plunger having first and second ends and having a shaft that extends through the bore, said shaft being movable along a longitudinal axis and having an expanded portion that prevents the stimulus plunger from sliding our of an opening in the housing; and
(iii) a compression spring that biases said second end of the stimulus plunger away from contact with the piezoelectric disk;

wherein the patient contacting portion is configured to activate, during the contact, the piezoelectric disk in the probe resulting in a signal response that identifies when an onset of the contact of the predetermined body area occurs;

wherein the signal response is used in identifying a subsequent collection of electrical responses from a plurality of electrodes placed on the patient's skin, wherein the collection is indicative of the bulbocavernosus muscle reflex or an absence thereof;

wherein the placed plurality of electrodes are spaced apart from each of: (i) an additional electrode for supplying a voltage to the patient's skin, and (ii) the predetermined body area contacted by the patient contacting portion for inducing the bulbocavernosus muscle reflex;

wherein one or more characteristics of the electrical responses in the collection provide information about the bulbocavernosus muscle reflex;

wherein the characteristics are determined using at least one of (a) through (d) following: (a) a time delay between the response and the collection are output with information, (b) a time duration for the collection, (c) a value indicative of a magnitude of at least one electrical response of the collection, and (d) a voltage differential between the electrical responses of the collection and a voltage indicative of the bulbocavernosus muscle substantially at rest.

2. The apparatus of claim 1, wherein: (i) the predetermined body area includes the patient's penis or the patient's clitoris, (ii) the characteristics are determined using at least most of (a) through (d), and (iii) the apparatus includes a computer for determining the characteristics, and an electronic display for displaying a graphical representation of the collection in graphical relation to a time of the signal response.

3. The apparatus of claim 1, wherein the piezoelectric disk is an electrical switch, wherein the signal response is a result of a mechanical effect of the contact on the piezoelectric disk for changing an electrical property thereof.

4. The apparatus of claim 2, wherein the piezoelectric disk is an electrical switch.

5. The apparatus of claim 4, wherein the force affects an electrical property of the piezoelectric disk.

6. The apparatus of claim 2, wherein for determining the characteristics, a voltage difference between two of the plurality of electrodes is determined.

7. The apparatus of claim 1, wherein the contact is non-invasive.

8. The apparatus of claim 1, wherein the first and second of the electrodes are placed on opposite sides of the patient's rectum, and adjacent thereto.

9. The apparatus of claim 1, wherein the patient contacting portion is separable from the remainder of the probe so that the probe is operably reusable when a different patient contacting portion is included therein, wherein each one of the patient contacting portion and the different patient contacting portion includes electronics for use in preventing a reuse of the one patient contacting portion;

wherein the electronics includes a data storage for identifying one of: (i) if the patient contacting portion therefor has been previously used with the probe for contacting a patient for inducing the bulbocavernosus reflex, and (ii) a length of time the patient contacting portion therefor has been activated by the probe.

10. The apparatus of claim 1, wherein the probe includes a data store for storing data indicative of a history of activation of the probe.

11. The apparatus of claim 10, wherein the data store is included in the patient contacting portion, and the patient contacting portion is movable relative to the housing when the force is applied to the predetermined body area.

12. The apparatus of claim 1, further including an analysis process for activating at least one predictive model, wherein upon receiving the characteristics, the at least one predictive model determines a correspondence between (i) the characteristics, and (ii) one of the following disorders: a neurological disorder, a sexual disorder, and a voiding dysfunction wherein the correspondence is determined according to a similarity between the characteristics and previously collected data indicative of the disorders.

13. The apparatus of claim 12, wherein the at least one predictive model determines a similarity between the characteristics, and one or more predetermined associations between a patient diagnosis, and collected information representative of (a) through (d) obtained from other patients.

14. The apparatus of claim 1, wherein the information is representative of (a).

15. The apparatus of claim 1, wherein the information is representative of (b).

16. The apparatus of claim 1, wherein the information is representative of (c).

17. The apparatus of claim 1, wherein the information is representative of (d).

18. The apparatus of claim 1, wherein the vibratory assembly vibrates in a range of 2 Hz to 20 Hz.

* * * * *